US00PP35477P2

(12) United States Plant Patent
Liu et al.

(10) Patent No.: US PP35,477 P2
(45) Date of Patent: Nov. 14, 2023

(54) ***NELUMBO* PLANT NAMED 'QINHUAI CHENWU'**

(50) Latin Name: *Nelumbo nucifera*
Varietal Denomination: QINHUAI CHENWU

(71) Applicants: Xiaojing Liu, Nanjing (CN); Fengfeng Du, Nanjing (CN); Dongrui Yao, Nanjing (CN); Shaozhou Chen, Nanjing (CN)

(72) Inventors: Xiaojing Liu, Nanjing (CN); Fengfeng Du, Nanjing (CN); Dongrui Yao, Nanjing (CN); Shaozhou Chen, Nanjing (CN)

(73) Assignee: Institute of Botany, Jiangsu Province and Chinese Academy of Science

( * ) Notice: Subject to any disclaimer, the term of this patent is extended or adjusted under 35 U.S.C. 154(b) by 0 days.

(21) Appl. No.: 18/095,434

(22) Filed: Jan. 10, 2023

(51) Int. Cl.
*A01H 6/00* (2018.01)
*A01H 5/02* (2018.01)

(52) U.S. Cl.
USPC ..... Plt./342

(58) Field of Classification Search
USPC ..... Plt./342
CPC ..... A01H 6/00; A01H 5/02
See application file for complete search history.

*Primary Examiner* — Keith O. Robinson
(74) *Attorney, Agent, or Firm* — Cassandra Bright

(57) ABSTRACT

A new and distinct cultivar of *Nelumbo* plant named 'QINHUAI CHENWU' is disclosed, characterized by abundant yellow-green double flowers. Flowers have a plate-like shape, with petals neatly arranged. The new variety is useful as both an ornamental plant and for cut flower production.

4 Drawing Sheets

Latin name of the genus and species: *Nelumbo nucifera*.
Variety denomination: 'QINHUAI CHENWU'.

BACKGROUND OF THE INVENTION

The new cultivar, *Nelumbo* 'QINHUAI CHENWU', is the product of a planned breeding program. The new variety originated from an open-pollination of the unpatented seed parent, *Nelumbo* 'Jinling Ningcui'. The pollen parent cannot be identified as the new variety was developed in an open-pollination program. The open-pollination was made during July of 2019 in Nanjing, Jiangsu province, China at a research nursery. The new cultivar 'QINHUAI CHENWU' was selected in June of 2020 at the same location.

Asexual reproduction of the new cultivar 'QINHUAI CHENWU' was first performed by root division in Jiangsu province, China at a research nursery April of 2021, *Nelumbo* 'QINHUAI CHENWU' has since produced multiple generations and has shown that the unique features of this cultivar are stable and reproduced true to type.

SUMMARY OF THE INVENTION

The cultivar 'QINHUAI CHENWU' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'QINHUAI CHENWU'. These characteristics in combination distinguish 'QINHUAI CHENWU' as a new and distinct *Nelumbo* cultivar:

1. Unique yellow-green flower color.
2. Double flowers with approximately 300 petals per flower.

3. Plate-shaped flower form, composed of attractively arranged, regularly whorled petals.
4. Green color of upper receptacle.
5. Broad ovate flower bud.
6. Seed pod with an attractive green color.
6. Flowering period of about 70 days, from mid-June to late August.
7. Flower density of approximately 20 to 26 flowers per square meter.

PARENTAL COMPARISON

Plants of the new cultivar 'QINHUAI CHENWU' are similar to plants of the seed parent in most horticultural characteristics. However, plants of the new cultivar 'QINHUAI CHENWU' differ in the following:

1. Flower color of the new variety is a deeper yellow-green than the flower color of the seed parent.
2. The new variety produces many more flowers than the seed parent.
3. Flowers of the new variety are double, while flowers of the seed parent are single.
4. The new variety has fewer stamens per flower than the seed parent.
5. Flower form of the new variety is plate-like, while the flower form of the seed parent is bowl-shaped.
6. Stamens of the new variety are partially petaloid, while stamens of the seed parent are normal.
7. Bud shape of the new variety is broad ovate, while bud shape of the seed parent is long ovate.

The pollen parent cannot be identified.

COMMERCIAL COMPARISON

The new cultivar 'QINHUAI CHENWU' can be compared to the unpatented commercial variety *Nelumbo*

'Xiangxuchai'. Plants of the new cultivar 'QINHUAI CHENWU' differ in the following:

1. Flower color of the new variety is yellow-green, while flower color of this comparator is white.
2. Flowers of the new variety produce many more petals than flowers of this comparator.
3. Receptacle of the new variety is green at the top, while receptacle of this comparator is yellow-green.
4. Bud shape of the new variety is broad ovate, while bud shape of this comparator is ovate.
5. Flowering period of the new variety is about 70 days, while flowering period of this comparator is about 56 days.
6. The new variety has higher flower density than this comparator.

BRIEF DESCRIPTION OF THE PHOTOGRAPHS

The accompanying photographs illustrate in full color typical plants of 'QINHUAI CHENWU' grown outdoors, in a pond, in Jiangsu province, China. The photographs were taken using conventional techniques and equipment. While the colors in these photographs may display variances of color as compared to the living cultivar, due to LRV (light reflectance value), they are as accurate as possible using conventional photographic techniques. Colors in the photographs may appear to differ slightly from the color values cited in the botanical description, which accurately describe the colors of the new *Nelumbo* plant. Temperatures ranged from approximately 20° C. to 30° C. night and about 25° C. to 38° C. during the day. No artificial light, photoperiodic treatments or chemical treatments were given to the plants.

DETAILED BOTANICAL DESCRIPTION

Figure 1:
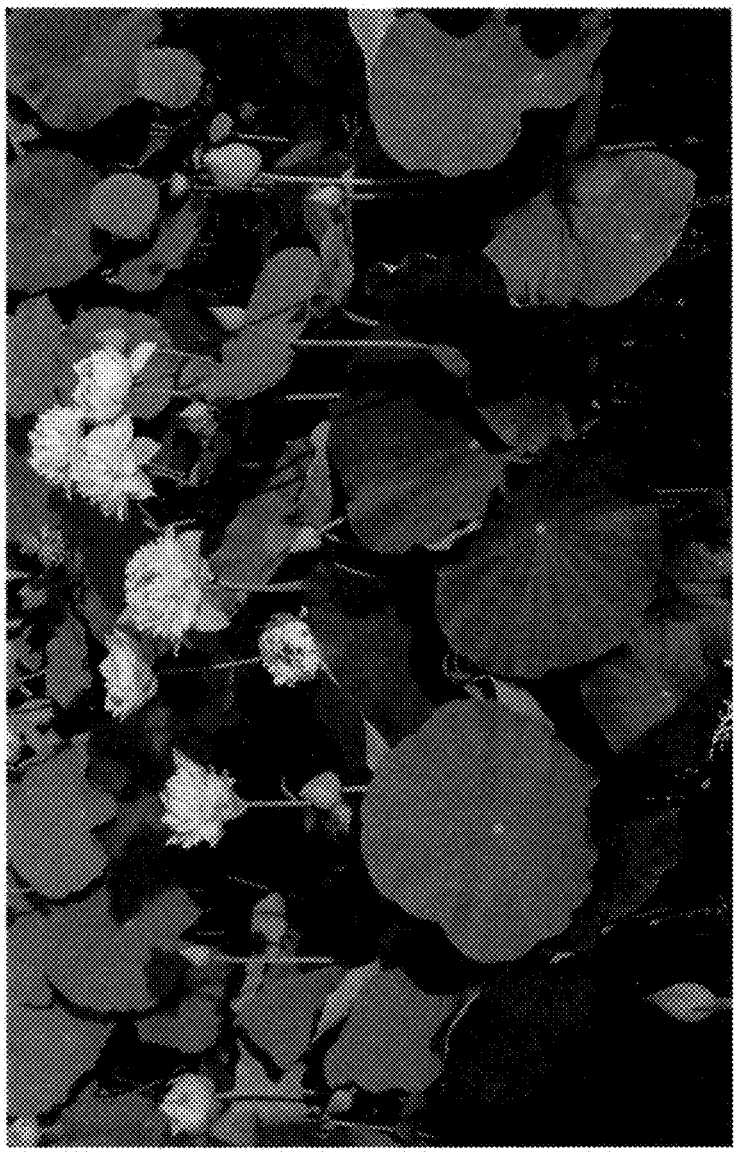
FIG. 1 illustrates in full color typical mature flowering of plants of *Nelumbo* 'QINHUAI CHENWU' at approximately 12 months.
Figure 2:
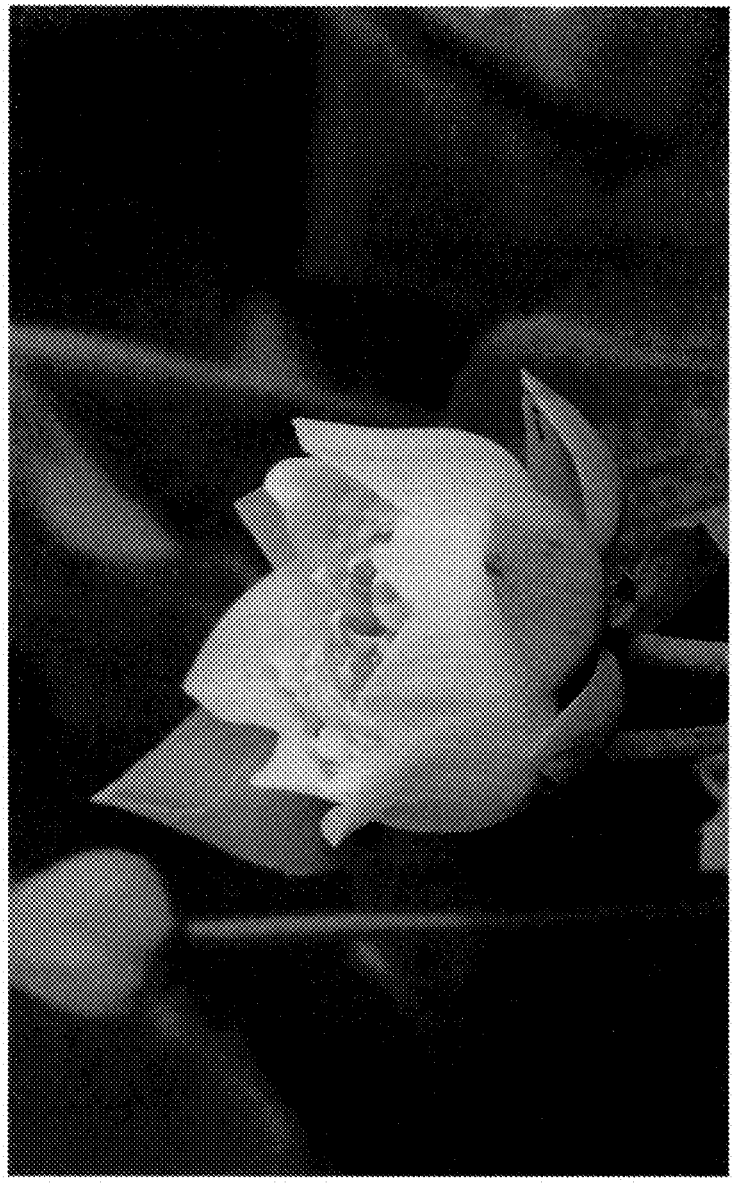
FIG. 2 illustrates in full color a typical flower of *Nelumbo* 'QINHUAI CHENWU' just emerging from the bud stage.
Figure 3:
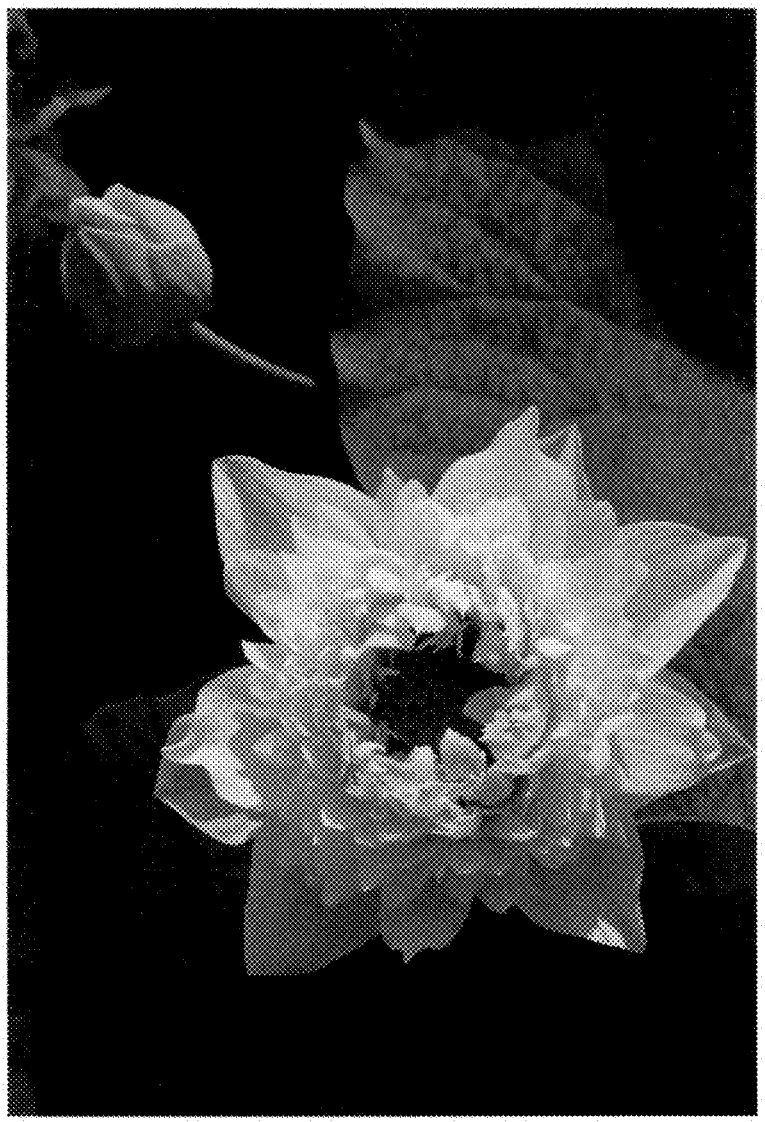
FIG. 3 illustrates in full color a top-view of a typical flower of *Nelumbo* 'QINHUAI CHENWU'.
Figure 4:
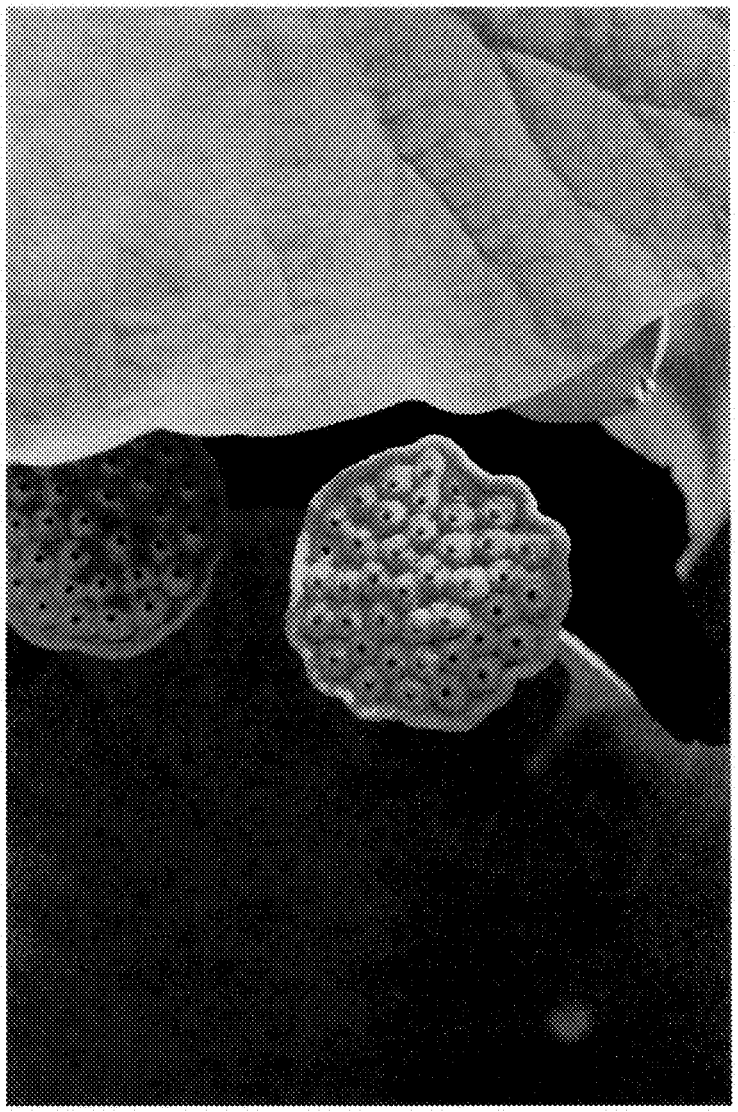
FIG. 4 illustrates in full color a typical seed pod of *Nelumbo* 'QINHUAI CHENWU'.

In the following description, color references are made to The Royal Horticultural Society Colour Chart, 2019, except where general terms of ordinary dictionary significance are used. The following observations and measurements describe 'QINHUAI CHENWU' plants grown in an outdoor pond in Jiangsu province, China. Average day temperature range was around 16° C. to 34° C.; average night temperature ranged around 13° C. to 28° C. No artificial light, photoperiodic treatments or chemical treatments were given to the plants. Natural light conditions were full sunlight. Measurements and numerical values represent averages of typical plant types.

Botanical classification: *Nelumbo nucifera* 'QINHUAI CHENWU'.

PROPAGATION

Type of propagation typically used: Root divisions.

Root description: Adventitious roots at the rhizome node. Moderately dense, moderately branching, medium thickness, fleshy texture. White in color, not accurately described with R.H.S. chart.

PLANT

Age of plant described: 1 year.

Container size of the plant described: In a pond of approximately 4 meters in length, 0.9 meters in width, and 25 cm in depth.

Growth habit: Heliophilous.

Height: Average 48 to 75 cm from soil to top of foliar plane; 65 to 88 cm from soil to top of floral plane.

Plant spread: Approximately 160×90 cm.

Growth rate: Moderate.

Plant vigor: High.

Branching habit: Sympodial, basal. No pinching required.

Primary branches per plant: 5 to 10.

Secondary branches per primary lateral branch: 3 to 5.

Lateral branch length: 70 to 90 cm.

Lateral branch diameter: 3 to 4 cm.

Internode length: 15 to 20 cm.

Stem:

*Shape/appearance*.—Rhizome, nodose, cylindrical. Underground stem.

*Aspect*.—Horizontal underground growth.

*Strength*.—Weak.

*Color*.—Developing: Near RHS Yellow-Green 145D. At Internodes: Near RHS Yellow-Green 145D. Developed: Near RHS Yellow 2C.

*Pubescence*.—None.

*Luster*.—Matte.

FOLIAGE

Leaf:

*Arrangement*.—Single leaf ranked, before and after flowering.

*Average length*.—Average 28 to 38 cm.

*Average width*.—24 to 33 cm.

*Shape of blade*.—Orbicular, peltate.

*Apex*.—Dimple.

*Base*.—Leaf stalk attached to center of lower surface of orbicular leaf.

*Margin*.—Entire, slightly undulate.

*Texture of top surface*.—Smooth.

*Texture of bottom surface*.—Smooth, cancellate.

*Pubescence*.—None.

*Color*.—Young foliage upper side: RHS Yellow-Green 143B. Young, foliage, under side: RHS Green 138C. Mature foliage upper side: RHS Green 138A. Mature foliage, under side: RHS Green 137A. Fall foliage upper side: RHS Greyed-Green 195B. Fall foliage, under side: RHS Greyed-Green 195C.

*Venation*.—Type: Reticulate. Venation color upper side: RHS Green 138D. Venation color under side: RHS Yellow-Green 144C.

Petiole:

*Length*.—Average range 47 cm to 63 cm.

*Diameter*.—Average range 0.5 cm to 0.9 cm.

*Color*.—Upper surface: RHS Yellow-Green 144B. Lower surface: RHS Yellow-Green 144B.

*Strength*.—Medium, stout.

*Texture.*—Small spines, found more densely at base.
*Form.*—Semi-woody, stiff, inside have vertical hollow and latex.
*Luster.*—Weak.

FLOWER

*Natural flowering season.*—Mid-June through late August.
*Flower type and habit.*—Single, double-layered flowers. Upright. Freely flowering habit.
*Flowers per plant.*—11 to 15.
*Buds per plant.*—7 to 9.
*Flower longevity on plant.*—5 to 6 days. Self-cleaning.
*Flower longevity as a cut flower.*—3 to 4 days.
*Flower size.*—Height: Approximately 14 to 16.2 cm. Width: Approximately 12 to 16 cm. Depth: 5.5 to 8 cm.
*Flower shape.*—Plate-shaped.

Bud:
*Shape.*—Broad ovate.
*Length.*—Approximately 6 to 7 cm.
*Diameter.*—Approximately 4.2 to 5.8 cm.
*Texture.*—Obvious veins.
*Luster.*—None.
*Color.*—RHS Yellow-Green 144B.

Petals:
*Arrangement.*—Verticillate.
*Quantity.*—295 to 339 per flower.
*Number of whorls.*—16.
*Fused.*—No.
*Margin.*—Entire.
*Shape.*—Obovate/oval.
*Apex.*—Acuminate.
*Base.*—Truncate.
*Texture.*—Papery, both surfaces.
*Rugosity.*—Smooth and weak.
*Luster.*—Weak, both sides.
*Petal length.*—6.7 to 8.2 cm.
*Petal width.*—2.5 to 5.5 cm.
*Color.*—When Opening: Upper Surface: RHS Yellow-Green 145C. Under Surface: RHS Yellow-Green 145B. Fully Opened: Upper Surface: RHS Yellow-Green 145C; venation 144B. Under Surface: RHS Yellow-Green 145C; venation 144B. Fading: Upper Surface: RHS Yellow-Green 150D. Under Surface: RHS Yellow-Green 150D.

Petaloids:
*Arrangement.*—Verticillate.
*Quantity.*—285 to 327 per flower.
*Number of whorls.*—12.
*Length.*—0.5 to 4.5 cm.
*Width.*—0.2 to 1.8 cm.
*Shape.*—Obovate-lanceolate.
*Margin.*—Entire.
*Apex.*—Apiculate.
*Base.*—Wedge.
*Texture.*—Papery, both surfaces.
*Rugosity.*—Smooth and weak.
*Luster.*—Weak, both sides.
*Color.*—When opening: Upper Suface: RHS Yellow 1D. Under Surface: RHS Yellow-Green 150C. Fully opened: Upper Surface: RHS Yellow 1D; venation 150C. Under Surface: RHS Yellow 1D; venation Yellow-Green 144C. Fading: Under Surface: RHS Yellow-Green 150D. Under Surface: RHS Yellow-Green 150D.

Sepals:
*Quantity.*—4.
*Arrangement.*—Verticillate.
*Calyx shape.*—Oval.
*Fused.*—No.
*Number of whorls.*—2.
*Length.*—2.6 to 4.2 cm.
*Width.*—1.2 to 2.8 cm.
*Shape.*—Ovoid.
*Apex.*—Acuminate.
*Margin.*—Entire.
*Base.*—Truncate.
*Texture.*—Papery, both sides.
*Luster.*—Weak, both sides.
*Color.*—When Opening: Upper Surface: RHS Yellow-Green 144D. Under Surface: RHS Green 143C. Fully Opened: Upper Surface: RHS Greyed-Green 195A. Under Surface: RHS Greyed-Green 197B.

Fragrance: Moderate strength, honey, floral scent.

Pedicel:
*Length.*—54 to 82 cm.
*Diameter.*—0.5 to 0.8 cm.
*Strength.*—Medium, stout.
*Texture.*—Semi-woody, stiff, inside vertical hollow and latex.
*Luster.*—Weak.
*Color.*—Near RHS Yellow-Green 145C.

REPRODUCTIVE ORGANS

Stamens: (Androecium).
*Number.*—30 to 89.
*Filament length.*—6.5 to 9 mm.
*Filament color.*—Near RHS Yellow2C.
*Anther length.*—9 to 10 mm.
*Anther width.*—1 to 1.5 mm.
*Anther color.*—Near RHS Yellow-Orange 22A.
*Anther shape.*—Bar.
*Pollen.*—Moderate.
*Pollen color.*—Near RHS Yellow-Orange 22A.

Pistil: (Gynoecium).
*Number.*—24 to 33.
*Length.*—9 to 11 mm.
*Stigma.*—Shape: Circular. Color: Near RHS Yellow-Green 145D. Style Length: 1.5 to 2 mm. Stigma Diameter: 1 to 1.5 mm. Style Color: Near RHS Yellow-Orange 22D. Ovary Color: Near RHS Yellow 2C.

OTHER CHARACTERISTICS

Seeds: Seed abortion.

Fruit:
*Quantity.*—24 to 36 per plant.
*Length.*—3 to 3.8 cm.
*Diameter.*—4.2 to 6.5 cm.
*Texture.*—Smooth.
*Color.*—Near RHS Green 137B.
*Taste.*—None.
*Days to ripen.*—21 to 40 days.

Root structures: Rhizomes.
*Shape.*—Cylindrical with nodes, expanded in winter.
*Length.*—80 to 110 cm.

*Diameter*.—0.5 to 3 cm.

*Texture*.—Fleshy.

*Color*.—Near RHS White 155A.

Temperature tolerance: Tolerates temperatures from approximately −10° C. to at least 40° C. High tolerance to rain; medium tolerance to wind. USDA hardiness zone 6A to 13B.

Disease/pest resistance: Medium resistance and susceptibility to normal diseases of *Nelumbo* observed. Medium resistance and susceptibility to normal pests of *Nelumbo* observed. The most common problem in Lotus is tuber deformation caused by the parasitic nematode *Hirschmanniella diversa* Sher and *H. imamur* Sher. Less commonly, leaf vein disease may also be seen, caused by *Nigrospora pyriformis*. Potential pests of Lotus include the waterlily aphid (*Rhopalosiphum nymphaeae*), red spider mite (*Tetranychus tumidus*) as well as thrips *Frankliniella schultzei Trybom* and *Scirtothrips dorsalis*.

What is claimed is:

1. A new and distinct cultivar of *Nelumbo* plant named 'QINHUAI CHENWU' as herein illustrated and described.

* * * * *